(12) United States Patent
Sorimoto et al.

(10) Patent No.: US 11,790,547 B2
(45) Date of Patent: Oct. 17, 2023

(54) INFORMATION PROCESSING APPARATUS AND DATA PROCESSING METHOD FOR PROCESSING DATA OBTAINED BY A SCANNER POSITIONALLY VARIABLE IN RELATION TO A SUBJECT

(71) Applicant: J. MORITA MFG. CORP., Kyoto (JP)

(72) Inventors: Keisuke Sorimoto, Kyoto (JP);
Masayuki Sano, Kyoto (JP)

(73) Assignee: J. MORITA MFG. CORP., Kyoto (JP)

(*) Notice: Subject to any disclaimer, the term of this patent is extended or adjusted under 35 U.S.C. 154(b) by 328 days.

(21) Appl. No.: 17/149,582

(22) Filed: Jan. 14, 2021

(65) Prior Publication Data
US 2021/0217189 A1 Jul. 15, 2021

(30) Foreign Application Priority Data

Jan. 15, 2020 (JP) .................................. 2020-004243

(51) Int. Cl.
*G06T 7/55* (2017.01)
*G06F 3/04847* (2022.01)
(Continued)

(52) U.S. Cl.
CPC ............ *G06T 7/55* (2017.01); *G06F 3/04847* (2013.01); *G06T 5/50* (2013.01); *G06T 7/0012* (2013.01); *G06T 2207/30036* (2013.01)

(58) Field of Classification Search
CPC ..................... G06T 7/55; G06T 7/0012; G06T 2207/30036; G06F 3/04847
(Continued)

(56) References Cited

U.S. PATENT DOCUMENTS

2006/0239521 A1 10/2006 Crucs
2015/0222878 A1 8/2015 Thiel et al.
(Continued)

FOREIGN PATENT DOCUMENTS

JP 2005-267677 A 9/2005
JP 2009-523547 A 6/2009
(Continued)

OTHER PUBLICATIONS

Japanese Office Action dated May 10, 2022 in Japanese Patent Application No. 2020-004243 (with English translation), 10 pages.
(Continued)

*Primary Examiner* — Gabriel I Garcia
(74) *Attorney, Agent, or Firm* — Oblon, McClelland, Maier & Neustadt, L.L.P.

(57) ABSTRACT

An information processing apparatus includes management circuitry that manages three-dimensional data obtained by a scanner in the order of obtaining, display controller circuitry that controls a display to show a three-dimensional image generated from combined data generated by combining a plurality of pieces of three-dimensional data, and input circuitry that accepts an operation by a user. When the input circuitry accepts an operation to select three-dimensional data, the management circuitry sets, from the selected three-dimensional data of last obtained three-dimensional data, data to be deleted. The display controller circuitry controls the display to show a three-dimensional image modified to exclude the data to be deleted.

13 Claims, 12 Drawing Sheets

(51) Int. Cl.
   *G06T 5/50*   (2006.01)
   *G06T 7/00*   (2017.01)
(58) Field of Classification Search
   USPC .......................................................... 382/154
   See application file for complete search history.

(56) References Cited

U.S. PATENT DOCUMENTS

| | | | | |
|---|---|---|---|---|
| 2017/0213354 | A1* | 7/2017 | Glinec | .................. G06T 7/55 |
| 2019/0231492 | A1* | 8/2019 | Sabina | ................ A61B 1/0646 |
| 2019/0269485 | A1* | 9/2019 | Elbaz | ................ A61B 1/00009 |
| 2020/0349705 | A1* | 11/2020 | Minchenkov | ........... G06T 17/00 |

FOREIGN PATENT DOCUMENTS

| | | |
|---|---|---|
| JP | 2010-532681 A | 10/2010 |
| JP | 2012-157683 A | 8/2012 |
| JP | 2015-147045 | 8/2015 |
| JP | 2017-536592 | 12/2017 |
| JP | 2018-509213 A | 4/2018 |
| JP | 2019-524367 A | 9/2019 |
| WO | WO 2007/084589 A2 | 7/2007 |
| WO | WO 2009/006303 A2 | 1/2009 |
| WO | WO 2016/142818 A1 | 9/2016 |
| WO | 2017/111116 A1 | 6/2017 |
| WO | WO 2018/038748 A1 | 3/2018 |
| WO | 2018/185972 A1 | 10/2018 |
| WO | WO 2019/034742 A1 | 2/2019 |

OTHER PUBLICATIONS

Extended European Search Report dated Jun. 14, 2021 in European Patent Application No. 21151558.0, 10 pages.
Dentsply Sirona, "Delete and re-scan areas with CEREC Omnicam," Retrieved from the Internet [URL: https://www.youtube.com/watch?v=kX21Nc0YirQ], XP054981868, Jun. 18, 2013, 1 page.
Sirona, "Sirona Dental CAD/CAM System CEREC SW Operator's Manual," Retrieved from the Internet [URL: https://assets.dentsplysirona.com/websites/my-cerec/en-us/Operators_Manual_CEREC_Software_USA.pdf], XP055810423, Apr. 2018, 143 pages.
Planmeca, "Planmeca Emerald™ User Manual," Retrieved from the Internet [URL: https://www.planmeca.com/globalassets/planmeca/1-planmeca-usa-moderinization/cadcam/dental-scanning/emerald/manuals/emerald-manual-15698200e.pdf], XP055810427, Mar. 1, 2019, 60 pages.
Notice of Refusal dated May 16, 2023, issued in corresponding Japanese patent application No. 2022-111191 (with English translation).

* cited by examiner

INFORMATION PROCESSING APPARATUS AND DATA PROCESSING METHOD FOR PROCESSING DATA OBTAINED BY A SCANNER POSITIONALLY VARIABLE IN RELATION TO A SUBJECT

BACKGROUND

Field

The present disclosure relates to an information processing apparatus that processes data obtained by a scanner variable in positional relation with a subject and a data processing method of processing the data.

Description of the Background Art

In the dental field, various apparatuses have been developed as image pick-up apparatuses that pick up images of the inside of a mouth cavity. For example, a scanner for obtaining three-dimensional (3D) data of teeth in the mouth cavity of a patient has been developed as the image pick-up apparatus. In using the scanner to scan the inside of the mouth cavity to obtain three-dimensional data of the entire dentition (dental arch), a user has to move the scanner along the dentition to change a measurement position and repeats measurement a plurality of times to obtain a large number of pieces of three-dimensional data at different positions, because a range of measurement by the scanner in one measurement is limited. By subjecting the large number of pieces of obtained three-dimensional data to coordinate transformation and synthesizing the data, the three-dimensional data of the entire dentition can be generated.

When a position of the scanner is suddenly displaced while three-dimensional data is being obtained at each position or when a movable object enters the measurement range, three-dimensional data may be distorted or data that causes noise may be introduced. Then, in synthesis of three-dimensional data, erroneous synthesis such as registration between three-dimensional data at an erroneous position is carried out.

Japanese National Patent Publication No. 2017-536592 discloses detection of an error in arrangement of an obtained 3D view with respect to an adjacent image in a 3D view synthesis method. This publication discloses highlighted representation of the detected error.

Japanese Patent Laying-Open No. 2015-147045 discloses formation of a kind of three-dimensional video images by sequentially showing obtained images.

SUMMARY

According to the technique disclosed in Japanese National Patent Publication No. 2017-536592, a user can readily identify a portion where measurement has failed. According to the technique disclosed in Japanese Patent Laying-Open No. 2015-147045, by checking the three-dimensional video images, a user can readily identify at which timing in a step of obtaining a plurality of pieces of three-dimensional data measurement has failed.

Neither of the techniques disclosed in Japanese National Patent Publication No. 2017-536592 and Japanese Patent Laying-Open No. 2015-147045, however, pay attention to editing of the portion where measurement has failed. When measurement fails, the user may conduct again measurement at the portion where failure occurred.

For example, when a user finds failure during mead the user suspends measurement, edits obtained data, and then starts again measurement. When an operation to edit obtained data is complicated, measurement takes a longer time. When a place where measurement is conducted is narrow, it becomes difficult to perform the editing operation. Therefore, the editing operation is desirably simplified.

The present embodiments were made in view of such circumstances, and an object thereof is to provide an information processing apparatus and a data processing method that simplify an operation to edit data obtained by a scanner.

According to an embodiment, an information processing apparatus that processes data obtained by a scanner variable in positional relation with a subject is provided. The information processing apparatus includes a manager that manages a plurality of pieces of data in an order of obtainment by the scanner, a display controller that controls a display apparatus to show a synthesized image generated by synthesizing the plurality of pieces of data managed by the manager, and an input unit that accepts an operation by a user. The input unit accepts an operation to select at least one piece of data among the plurality of pieces of data managed by the manager. The manager sets data from the selected data to the last obtained data as data to be deleted. The display controller controls the display apparatus to show the synthesized image generated from data to be used except the data to be deleted, among the plurality of pieces of data managed by the manager.

According to an embodiment, a data processing method of processing data obtained by a scanner variable in positional relation with a subject is provided. The data processing method includes (a) managing a plurality of pieces of data in an order of obtainment by the scanner, (b) accepting an operation to select at least one piece of data among a plurality of pieces of managed data, (c) setting data from the selected data to the last obtained data as data to be deleted, and (d) showing on a display apparatus, a synthesized image generated by synthesizing data to be used except the data to be deleted, among the plurality of pieces of managed data.

The foregoing and other objects, features, aspects and advantages of the present disclosure will become more apparent from the following detailed description of the present disclosure when taken in conjunction with the accompanying drawings.

DETAILED DESCRIPTION

Figure 1:
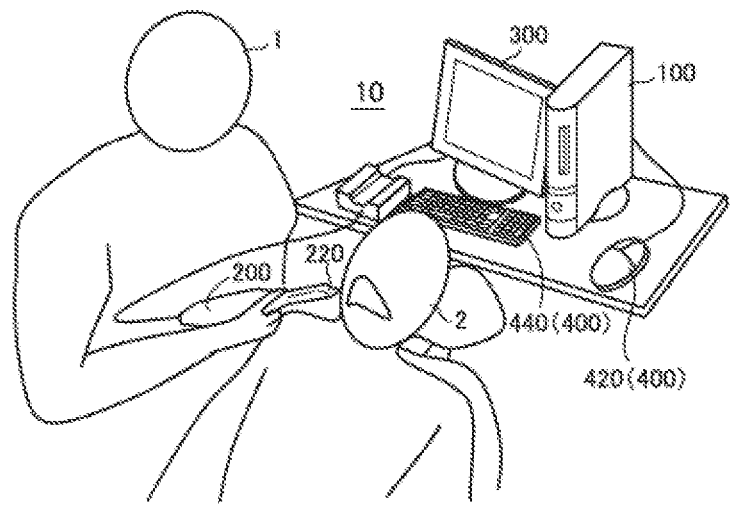
FIG. 1 is a schematic diagram showing an application of an information processing apparatus 100 according to the present embodiment.

An embodiment will be described in detail with reference to the drawings. The same or corresponding elements in the drawings have the same reference characters allotted and description thereof will not be repeated

[Application]

Figure 2:
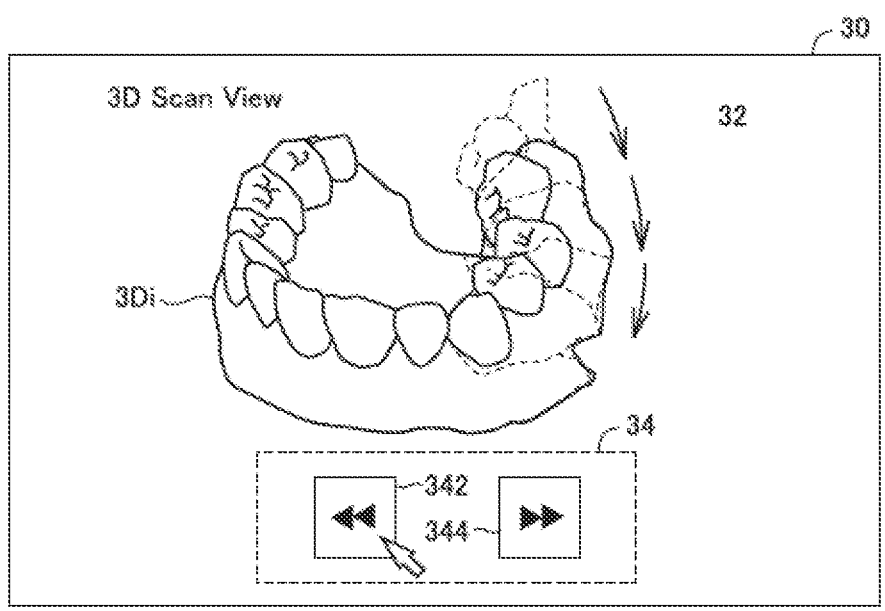
FIG. 2 shows an exemplary measurement screen 30 shown on a display 300 in information processing apparatus 100 according to the present embodiment.

An application of an information processing apparatus 100 according to the present embodiment is shown with reference to FIGS. 1 and 2. FIG. 1 is a schematic diagram showing an application of information processing apparatus 100 according to the present embodiment.

As shown in FIG. 1, a user 1 can obtain data on a three-dimensional shape (three-dimensional data) of the inside of the mouth cavity including teeth of an object 2 by using a scanner system 10. Anyone that uses scanner system 10 such as an operator including a dentist, a dental assistant, a teacher or a student at a dental university, a dental mechanic, an engineer of a manufacturer, or a worker in a manufacturing factory may be defined as the "user". Anyone for which scanner system 10 is used such as a patient of a dental clinic or a subject at a dental university may be defined as an "object". The "object" is not limited to a living person but may be a manikin, a model of a head, an animal other than human being, or a fossil.

Scanner system 10 according to the present embodiment includes information processing apparatus 100, a scanner 200, a display 300, and an input apparatus 400.

Scanner 200 obtains three dimensional data of an object to be scanned (an object) with a built-in three-dimensional camera. Specifically, scanner 200 scans the inside of the mouth cavity to obtain as three-dimensional data, positional information (coordinates on an axis in each of a vertical direction, a lateral direction, and a height direction) of each of a plurality of points that constitute teeth to be scanned, with an optical sensor.

The three-dimensional data is data including at least position information of each of a plurality of coordinate points or a plurality of textured surfaces that define a shape of a measured object. In the present embodiment, description will be given assuming that one unit of data referred to as three-dimensional data refers to data obtained in one measurement.

Information processing apparatus 100 generates a three-dimensional image based on the three-dimensional data obtained by scanner 200 and shows the generated three-dimensional image on display 300. The three-dimensional image means a two-dimensional projection viewed in a specific direction, of three-dimensional data (which is also referred to as combined data below) that is obtained by combining a plurality of pieces of three-dimensional data and covers a range wider than a measurement range that scanner 200 can cover in one measurement.

The measurement range that scanner 200 can cover in one measurement is dependent on a size of a probe 220 of scanner 200 that can be inserted into the mouth cavity, and it is generally a range approximately from one tooth to two teeth. Therefore, when three-dimensional data of the entire dentition (dental arch) within the mouth cavity is desired, user 1 has to change a position of measurement by moving scanner 200 along the dentition, repeat measurement a plurality of times, and obtain a large number of pieces of three-dimensional data at different positions.

Three-dimensional data is thus successively obtained by scanner 200. Information processing apparatus 100 successively generates three-dimensional images based on the obtained three-dimensional data. At this time, information processing apparatus 100 generates new combined data by combining new three-dimensional data with generated combined data, generates a three-dimensional image based on the generated new combined data, and shows the generated three-dimensional image an display 300. A series of processes to combine a plurality of pieces of three-dimensional data to generate combined data and to generate a three-dimensional image based on the combined data is simply referred to as "synthesis".

In scanner system 10 according to the present embodiment, user 1 should obtain a plurality of pieces of three-dimensional data while the user changes relative positional relation between a measured object and scanner 200. When relative positional relation between scanner 200 and the measured object suddenly changes while three-dimensional data is being obtained or when a movable object eaters a range of measurement by scanner 200 while three-dimensional data is being obtained, the three-dimensional data is distorted or data that causes noise in synthesis processing is introduced. Therefore, processing for synthesizing subsequently obtained three-dimensional data may fail. In this case, user 1 has to designate a portion where the user failed in obtaining three-dimensional data, delete the designated portion, and conduct measurement again with scanner 200.

Relying on a three-dimensional image shown on display 300, user 1 has to operate input apparatus 400 such as a mouse 420 or a keyboard 440 and perform such an editing operation to designate a portion where the user has failed in obtaining three-dimensional data.

In a clinical space where user 1 uses scanner 200, a wide space cannot necessarily be secured. Therefore, when the editing operation is complicated, the operation is difficult. In addition, user 1 operates summer 200 generally with his/her dominant hand. Therefore, when the editing operation is complicated, the user has to once release scanner 200 and to perform the operation by holding the mouse or the like again with the dominant band.

In the dental field, during measurement, an operator's hand or finger may be contaminated by bacteria or viruses due to contact with the inside of the mouth cavity of a patient. Therefore, it is not hygienically preferable for the operator to touch a peripheral device such as the mouse or the display when the operator suspends measurement and performs the operation to edit data. When a complicated editing operation is required, there are more occasions to touch the peripheral devices. Therefore, a simplified editing operation is demanded.

Information processing apparatus 100 according to the present embodiment accepts selection in a unit of three-dimensional data, sets data from selected three-dimensional data to last obtained three-dimensional data as data to be deleted, and shows on display 300, a three-dimensional image synthesized from data to be used except the data to be deleted, of the obtained three-dimensional data. Each of the data to be deleted and the data to be used includes at least one piece of three-dimensional data.

By thus selecting specific three-dimensional data, data from the selected three-dimensional data to the last obtained three-dimensional data is set as the data to be deleted, and hence selection of the data to be deleted is easy. Since the three-dimensional image is generated from the data to be used except the data to be deleted, a three-dimensional image generated when the data to be deleted is actually deleted can be checked, and the data to be deleted can readily be selected. Since the user can thus select data to be deleted in a unit of three-dimensional data while the user checks a shown three-dimensional image, the editing operation can be simplified.

FIG. 2 shows an exemplary measurement screen 30 shown on display 300 in information processing apparatus 100 according to the present embodiment. Measurement screen 30 is a user interface provided by information processing apparatus 100, and includes information obtained by scanner 200 and a selection tool for accepting an operation by a user. Measurement screen 30 shown in FIG. 2 is by way of example, and the user interface provided by information processing apparatus 100 is not limited thereto.

Measurement screen 30 includes a display area 32 where a three-dimensional image (synthesized image) is shown and a selection area 34 where a selection tool for selecting three-dimensional data is shown.

Information processing apparatus 100 shows a three-dimensional image 3Di synthesized from one piece of three-dimensional data or a plurality of pieces of three-dimensional data in display area 32.

As user 1 uses input apparatus 400 such as mouse 420 to operate the selection tool within selection area 34, information processing apparatus 100 accepts selection of three-dimensional data.

Information processing apparatus 100 provides user 1 with a selection tool that allows selection of data in an order reverse to the order of obtainment (which is also simply referred to as a "reverse order" below). The selection tool includes a back button 342 for successively changing selected three-dimensional data in the reverse order and a forward button 344 for changing selected three-dimensional data in the order of obtainment.

Back button 342 is a selection tool for changing selected three-dimensional data in the reverse order in a unit of one piece of three-dimensional data or a wait of a plurality of pieces of three-dimensional data. For example, when change is made one by one, last obtained three-dimensional data is selected at the time when back button 342 is operated once, and each time beck button 342 is thereafter operated, a selected object is changed one by one in the reverse order. Alternatively, when change is made five by five, three-dimensional data obtained last but four is selected at the time when back button 342 is operated once, and each time back button 342 is thereafter operated, a selected object is changed five by five in the reverse order.

Each time back button 342 is operated, information processing apparatus 100 shows in display area 32, three-dimensional image 3Di synthesized from three-dimensional data except data from three-dimensional data selected by the operation to last obtained three-dimensional data, among a plurality of pieces of obtained three-dimensional data.

For example, when back button 342 is operated, successive disappearance of three-dimensional images from a view along a direction shown with an arrow in FIG. 2 is shown in display area 32. In other words, in display area 32, reverse reproduction of obtainment of three-dimensional data is shown.

Forward button 344 is a selection tool for changing selected three-dimensional data in a unit of one piece or a plurality of pieces of three-dimensional data in the order of obtainment. When forward button 344 is operated, selected three-dimensional data is changed in the order of obtainment, with currently selected three-dimensional data being defined as the reference. In an example where change is made one by one, when forward button 344 is operated once while three-dimensional data obtained last but four is selected, the selected object is changed to three-dimensional data obtained last but three. Alternatively, in an example where change is made five by five, when forward button 344 is operated once while three-dimensional data obtained last but nine is selected, the selected object is changed to three-dimensional data obtained last but four.

Each time the selected object is changed by the operation onto forward button 344, information processing apparatus 100 generates three-dimensional image 3Di and shows the three-dimensional image in display area 32.

When back button 342 is operated, the number of pieces of three-dimensional data included in data to be deleted increases, and when forward button 344 is operated, the number of pieces of three-dimensional data included in data to be deleted decreases.

Thus, information processing apparatus 100 provides the selection tool (back button 342 and forward button 344) for changing in a snit of one piece of three-dimensional data or a plurality of pieces of three-dimensional data, data to be included in data to be deleted among a plurality of pieces of three-dimensional data obtained by scanner 200. User 1 can readily select data to be deleted by operating the provided selection tool.

Furthermore, information processing apparatus 100 shows in display area 32, a three-dimensional image synthesized from data to be used except data to be deleted that is selected by using the selection tool, among the plurality of pieces of obtained three-dimensional data. Therefore, since three-dimensional image 3Di shown in display area 32 is also changed in accordance with an operation onto the provided selection tool, user 1 can readily identify a portion where failure in obtaining three-dimensional data occurred

[Hardware Configuration of Information Processing Apparatus 100]

Figure 3:
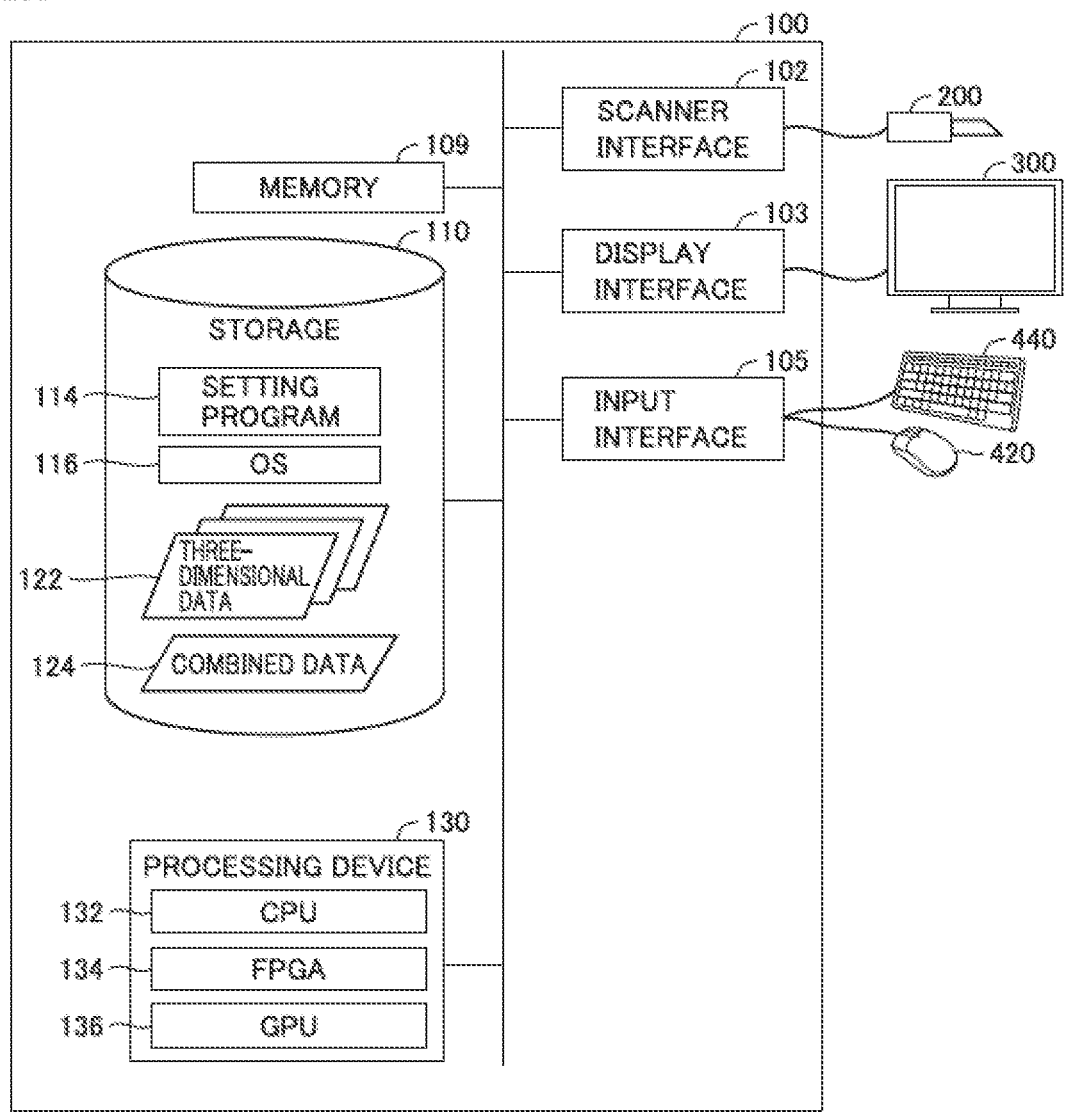
FIG. 3 is a schematic diagram showing a hardware configuration of information processing apparatus 100 according to the present embodiment.

An exemplary hardware configuration of information processing apparatus 100 according to the present embodiment will be described with reference to FIG. 3. FIG. 3 is a schematic diagram showing a hardware configuration of information processing apparatus 100 according to the present embodiment. Information processing apparatus 100 may be implemented, for example, by a general-purpose computer or a computer dedicated for scanner system 10.

As shown in FIG. 3, information processing apparatus 100 includes, as main hardware components, a scanner interface 102, a display interface 103, an input interface 105, a memory 109, a storage 110, and a processing device 130.

Scanner interface 102 is an interface for connection of scanner 200 and allows input and output of data between information processing apparatus 100 and scanner 200.

Display interface 103 is an interface for connection of display 300 and allows input and output of data between information processing apparatus 100 and display 300. Display 300 is implemented, for example, by a liquid crystal display (LCD) or an organic electroluminescence (EL) display.

Input interface 105 is an interface for connection of input apparatus 400 including mouse 420 and keyboard 440 and allows input and output of data between information processing apparatus 100 and input apparatus 400.

Though not shown, information processing apparatus 100 may include a medium reader, a removable disc, a network adapter, a speaker, a license authentication key, and a power supply.

Memory 109 provides a storage area where a program code or a work memory is temporarily stored in execution of an arbitrary program by processing device 130. Memory 109 is implemented by a volatile memory device such as a dynamic random access memory (DRAM) or a static random access memory (SRAM).

Storage 110 provides a storage area where various types of data necessary for processing for showing measurement screen 30 on display 300 are stored. Storage 110 is implemented by a non-volatile memory such as a hard disk or a solid state drive (SSD).

Storage 110 stores a setting program 114, an operating system (OS) 116, three-dimensional data 122, and combined data 124.

Setting program 114 is a program for performing processing for showing measurement screen 30 and processing for updating contents displayed on measurement screen 30.

Three-dimensional data 122 is data sent from scanner 200. Combined data 124 is data generated by combining a plurality of pieces of three-dimensional data 122.

Processing device 130 is an operation entity that performs various types of processing by executing various programs and represents an exemplary computer. Processing device 130 is configured, for example, with a central processing unit (CPU) 132, a field-programmable gate army (FPGA) 134, and a graphics processing unit (GPU) 136.

[Configuration of Scanner 200]

Figure 4:
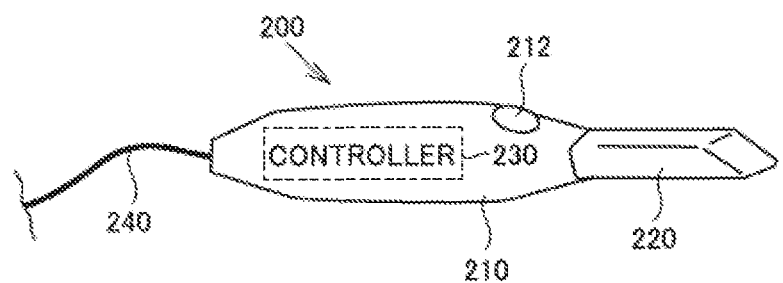
FIG. 4 is a schematic diagram of a scanner 200.

Scanner 200 will be described with reference to FIG. 4. FIG. 4 is a schematic diagram of scamper 200. Scanner 200 includes a housing 210, a probe 220 removably attached to a tip end of housing 210, and a controller 230. Scanner 200 is electrically connected to information processing apparatus 100 through a cable 240. Scanner 200 and information processing apparatus 100 may be connected to each other via wireless communication or via an optical cable partially or entirely.

Housing 210 corresponds to a handle portion held by user 1. In other words, scanner 200 is a hand-held scanner. Housing 210 is provided with an acceptance portion 212 that accepts an operation by user 1. Though a single button that protrudes from housing 210 is provided as acceptance portion 212, a single capacitance type touch panel or a single dial may be provided as acceptance portion 212. Alternatively, a plurality of buttons may be provided as acceptance portion 212.

In the present embodiment, acceptance portion 212 accepts start and stop (suspension) of measurement. Specifically, acceptance portion 212 functions as a stop button during measurement and functions as a start button while measurement is not conducted.

Controller 230 is configured with a CPU, a read only memory (ROM), and a random access memory (RAM). Specifically, the CPU reads various processing programs stored in the ROM, develops a processing program on the RAM, and proceeds with processing in accordance with the developed program, so that controller 230 controls the entire scanner 200 based on an operation by a user accepted at acceptance portion 212. Some or all of functions of controller 230 may be performed by dedicated hardware circuitry (for example, an application specific integrated circuit (ASIC) or an FPGA).

Though not shown, scanner 200 includes an optical component (a pattern generation element) and a light source for generating a pattern to be projected onto a measured object, a lens component for forming an image of the pattern on a surface of the measured object, a variable focus portion capable of changing a focal position, and an optical sensor (a CCD image sensor or a CMOS image sensor) for image pick-up of the projected pattern. Scanner 200 may obtain a three-dimensional shape based on the principles of the focusing method. Alternatively, scanner 200 may obtain a three-dimensional shape based on other principles, for example, with such techniques as the conform method, the triangulation method, white light interferometry, the stereo method, photogrammetry, simultaneous localization and mapping (SLAM), or optical coherence tomography (OCT). Scanner 200 may employ any principles so long as it obtains a three-dimensional shape with an optical approach.

[Method of Using Scanner 200]

Figure 5:
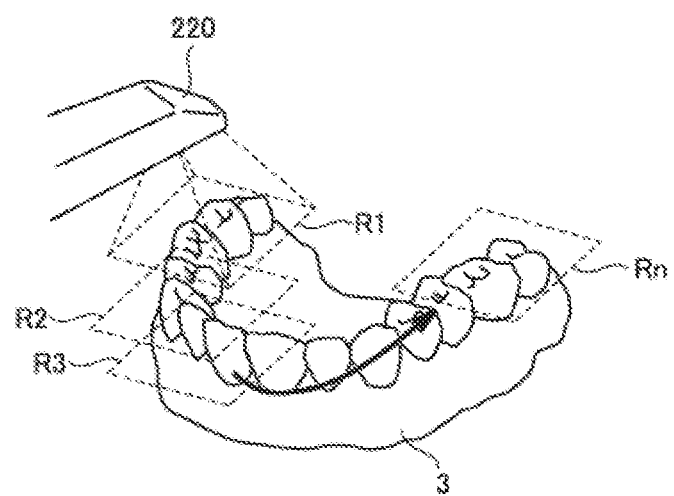
FIG. 5 is a diagram for illustrating a method of using scanner 200.

FIG. 5 is a diagram for illustrating a method of using scanner 200. As described above, a range of measurement by scanner 200 is dependent on a size of probe 220 of scanner 200 that can be inserted in the mouth cavity. Therefore, user 1 inserts probe 220 into the mouth cavity and obtains a large member of pieces of data at different positions by changing relative positional relation between scanner 200 and an object 3. More specifically, user 1 obtains a large number of pieces of three-dimensional data at different positions by successively changing the measurement range in the order of R1, R2, R3, . . . , and Rn by moving scanner 200.

Each time scanner 200 obtains three-dimensional data, it transmits obtained three-dimensional data to information processing apparatus 100.

[Exemplary Functional Configuration of Information Processing Apparatus 100]

Figure 6:
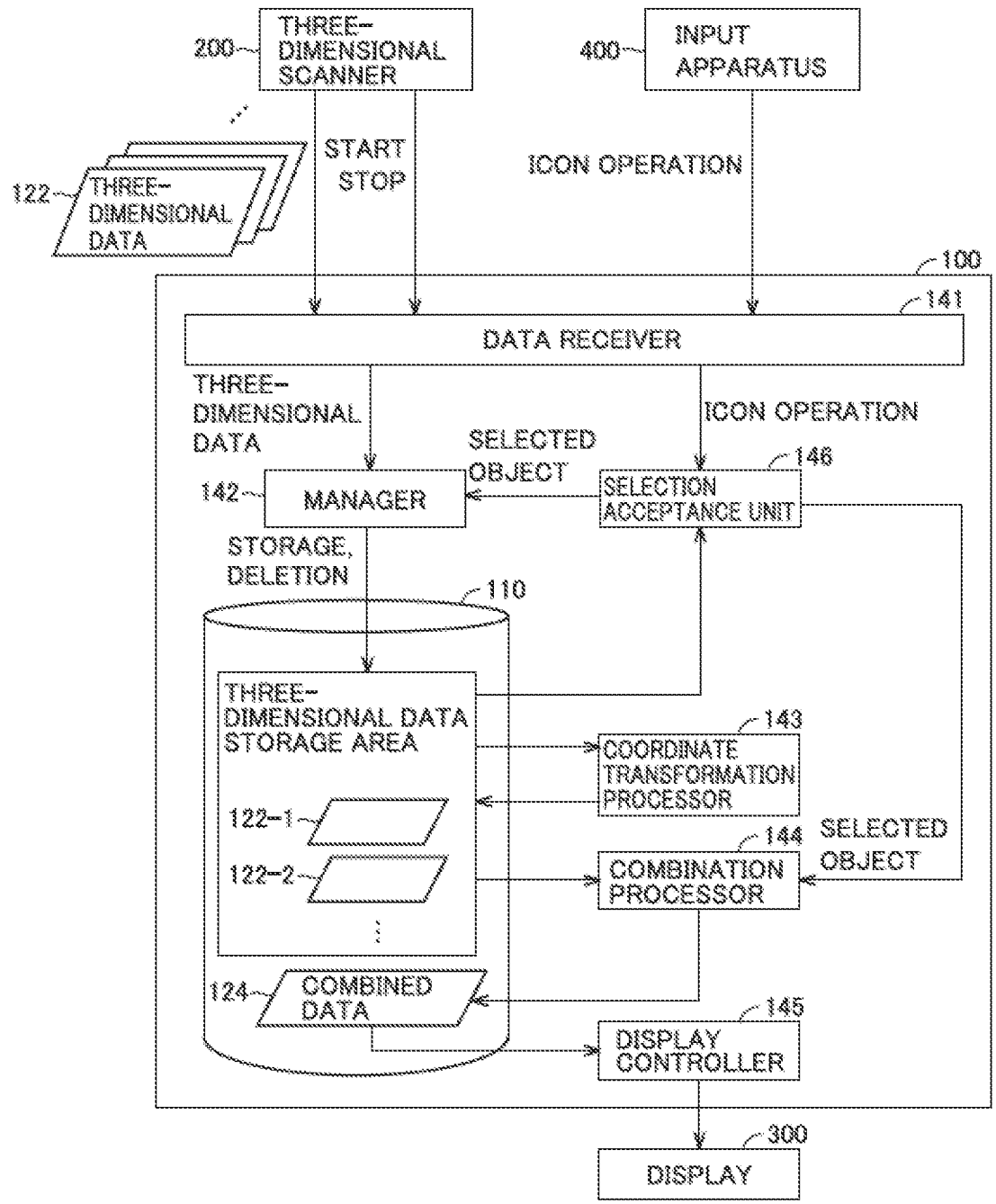
FIG. 6 is a diagram showing an exemplary functional configuration of information processing apparatus 100.

A function performed by execution of various programs by information processing apparatus 100 according to the present embodiment will be described with reference to FIG. 6. FIG. 6 is a diagram showing an exemplary functional configuration of information processing apparatus 100.

Information processing apparatus 100 includes a data receiver 141, a manager 142, a coordinate transformation processor 143, a combination processor 144, a display controller 145, and a selection acceptance unit 146.

Data receiver 141 accepts input of information from scanner 200 and input of data from input apparatus 400. Specifically, data receiver 141 accepts input of three-dimensional data 122 sent from scanner 200. When acceptance portion 212 of scanner 200 is operated to instruct scanner 200 to start or stop measurement, controller 230 of scanner 200 notifies information processing apparatus 100 of start or stop of measurement.

Manager 142 manages three-dimensional data 122 sent from scanner 200. Specifically, manager 142 has storage 110 successively store three-dimensional data 122 sent from scanner 200. Manager 142 identifies three-dimensional data 122 to be deleted (data to be deleted) based on information accepted by selection acceptance unit 146, and deletes at prescribed timing, three-dimensional data 122 confirmed as not to be used.

"Deletion" may encompass not only complete deletion of data but also movement of data to a storage area different from a recording area where three-dimensional data to be used is stared. In other words, "deletion" means deletion or movement from the storage area where three-dimensional data to be used is stored.

Manager 142 manages three-dimensional data 122 in the order of transmission from scanner 200. As described with reference to FIG. 5, each time scanner 200 obtains three-dimensional data, it traits the obtained three-dimensional data to information processing apparatus 100. In other words, manager 142 manages three-dimensional data 122 in the order of obtainment. It is assumed with reference to FIG. 5 that, with the measurement range being successively changed in the order of R1, R2, R3, . . . , and Rn, measurement is conducted for each of measurement ranges R1, R2, R3, . . . , and Rn and three-dimensional data 122 is obtained. A result of measurement in measurement range R1 is denoted as three-dimensional data 122-1 and a result of measurement in measurement range R2 is denoted as three-dimensional data 122-2. Manager 142 manages three-dimensional data 122-1 as data obtained first and manages three-dimensional data 122-2 as data obtained second.

Though it is assumed that three-dimensional data 122 is transmitted from scanner 200 to information processing apparatus 100 each time three-dimensional data 122 is obtained, a frequency of transmission is not limited as such. For example, scanner 200 may collectively transmit a plurality of pieces of three-dimensional data 122. In this case, scanner 200 preferably transmits three-dimensional data 122 such that the order of obtainment is recognizable.

Coordinate transformation processor 143 matches a coordinate system of each piece of three-dimensional data 122 sent from stonier 200 with a coordinate system for which a predetermined position is defined as the reference. Three-dimensional data 122 sent from scanner 200 includes at least position information (a coordinate on an axis in each of the vertical direction, the lateral direction, and the height direction) of each of a plurality of coordinate points or a plurality of textured surfaces that define object 3. Three-dimensional data 122 may include color information of each of the plurality of coordinate points or the plurality of textured surfaces, information on a vector normal to the textured surface, infatuation indicating time of photo shooting, or data of an individual model of a photo shooting apparatus.

The coordinate system of position information included in three-dimensional data 122 sent from scanner 200 is the coordinate system for which scanner 200 is defined as the reference. In other words, at the time point immediately after scanning, a position or a posture of the scanner at the time of obtainment of each piece of three-dimensional data 122 by scanning is different, and hence each piece of data is different in coordinate system. Therefore, normal combined data 124 is not obtained simply by aligning three-dimensional data 122 in states as they are. In order to obtain normal combined data 124, coordinate transformation processor 143 extracts a feature portion common among pieces of three-dimensional data 122 and determines a coordinate transformation matrix for coordinate transformation of the coordinate system of the position information such that common feature portions match with each other.

Figure 7:
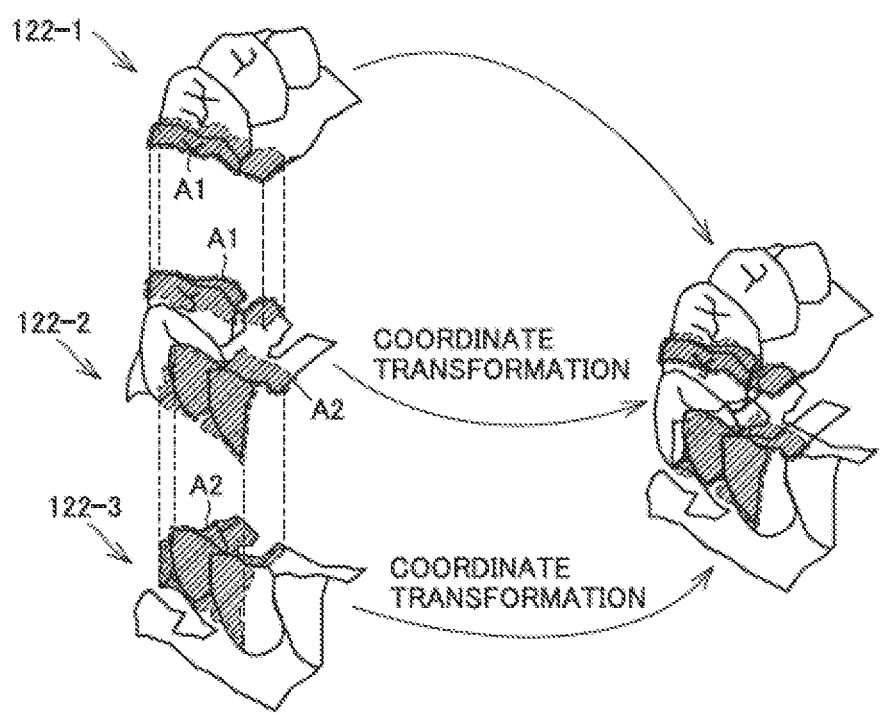
FIG. 7 is a diagram for illustrating coordinate transformation.

FIG. 7 is a diagram for illustrating coordinate transformation. Coordinate transformation processor 143 extracts a feature portion common between pieces of three-dimensional data 122 from each of three-dimensional data 122-1, three-dimensional data 122-2, and three-dimensional data 122-1. For example, in the example shown in FIG. 7, coordinate transformation processor 143 is assumed to extract a feature portion A1 common between three-dimensional data 122-1 and three-dimensional data 122-2 and a feature portion A2 common between three-dimensional data 122-2 and three-dimensional data 122-3.

Coordinate transformation processor 143 subjects the coordinate system of three-dimensional data 122-2 to coordinate transformation such that feature portion A1 of three-dimensional data 122-1 matches with feature portion A1 of three-dimensional data 122-2. Coordinate transformation processor 143 subjects the coordinate system of three-dimensional data 122-3 to coordinate transformation such that feature portion A2 of three-dimensional data 122-2 matches with feature portion A2 of three-dimensional data 122-3. An example where the coordinate system of newly obtained three-dimensional data is transformed with the coordinate system of three-dimensional data obtained in the past being defined as the reference is shown. Processing may be performed in the other way, that is, the coordinate system of three-dimensional data obtained in the past may be transformed with the coordinate system of newly obtained three-dimensional data being defined as the reference.

Coordinate transformation processor 143 determines in the order of obtainment, a coordinate transformation matrix for three-dimensional data 122 sent from scanner 200. Processing for matching the coordinate systems by coordinate transformation of three-dimensional data 122 sent from scanner 200 is also referred to as registration processing. The registration processing can be performed, for example, based on such techniques as matching processing using an iterative closest point (ICP) algorithm or various three-dimensional feature values (SHOT, PPF, and PFH).

Three-dimensional data 122 stored in storage 110 may be data subjected to coordinate transformation, information obtained by associating data yet to be subjected to coordinate transformation with a coordinate transformation maxis, or information obtained by associating data yet to be subjected to coordinate transformation, data subjected to coordinate transformation, and a coordinate transformation matrix with one another. In the present embodiment, description is given assuming that three-dimensional data 122 stored in storage 110 is data subjected to coordinate transformation.

Manager 142 may have data subjected to coordinate transformation stored, by having coordinate transformation processor 143 perform registration processing before it is stored in storage 110. Alternatively, when a plurality of pieces of three-dimensional data 122 are collectively transmitted from scanner 200, manager 142 may perform registration processing onto the plurality of collectively transmitted pieces of three-dimensional data 122 and may combine the plurality of collectively transmitted pieces of three-dimensional data 122 in a unit of a plurality of pieces and have storage 110 store the combined three-dimensional data. Though an example where various pieces of three-dimensional data 122 are stored in storage 110 which is a non-volatile memory is described, the three-dimensional data may be stored in a volatile memory or another storage area (a removable disc or another computer or a loud storage connected over a network).

Referring back to FIG. 6, combination processor 144 synthesizes a plurality of pieces of three-dimensional data 122 to generate combined data 124. Combination processor 144 synthesizes the plurality of pieces of three-dimensional data 122 to generate combined data 124 as three-dimensional data that coven a wider range than three-dimensional data of a measurement range.

Display controller 145 generates a three-dimensional image based on the three-dimensional data which is combined data 124 and controls display 300 to show the three-dimensional image. More specifically, the display controller calculates a two-dimensional projection when combined data 124 is viewed in a specific direction and controls display 300 to show the obtained two-dimensional projection. For calculation of the two-dimensional projection, for example, an algorithm for perspective projection, parallel projection, or the hide can be used. Display controller 145 controls display 300 to show measurement screen 30 described with reference to FIG. 2.

Selection acceptance unit 146 accepts selection of three-dimensional data based on an input operation through input apparatus 400. More specifically, selected three-dimensional data 122 is identified based on an operation onto the selection tool in selection area 34 and on operation contents and three-dimensional data 122 stored in storage 110. Selection acceptance unit 146 gives a notification about selected three-dimensional data 122 to each of manager 142 and combination processor 144.

Manager 142 sets as data to be deleted, data from selected three-dimensional data 122, the notification about which was given, to last obtained three-dimensional data 122. Manager 142 deletes the set data to be deleted in response to a deletion instruction. In the present embodiment, the deletion instruction includes start of measurment. When manager 142 is notified of start of measurement and data is newly obtained, manager 142 deletes three-dimensional data 122 to be deleted.

Normally, user 1 starts to newly obtain data after it confirms data to be deleted. Therefore, by deleting three-dimensional data 122 to be deleted at the time when obtainment of data is started and data is newly obtained, user 1 does not have to take the trouble to give a deletion instruction so that an operation by user 1 can be simplified.

Combination processor 144 generates combined data 124 based on the notification about selected three-dimensional data 122. Combination processor 144 sets as three-dimensional data to be combined, three-dimensional data 122 included in data to be used except data to be deleted set by manager 142 among pieces of three-dimensional data 122 obtained so far. Display controller 145 generates a three-dimensional image based on generated combined data 124 and controls display 300 to show the three-dimensional image. User 1 can thus check the three-dimensional image generated based on data set as the data to be used.

[Processing During Measurement, During Suspension, and after Resumption]

Information processing apparatus 100 is notified of start of measurement or stop of measurement from scanner 200. Therefore, information processing apparatus 100 can identify whether or not measurement is currently being conducted. A state that measurement is not being conducted is also referred to as "during suspension" below.

Figure 8:
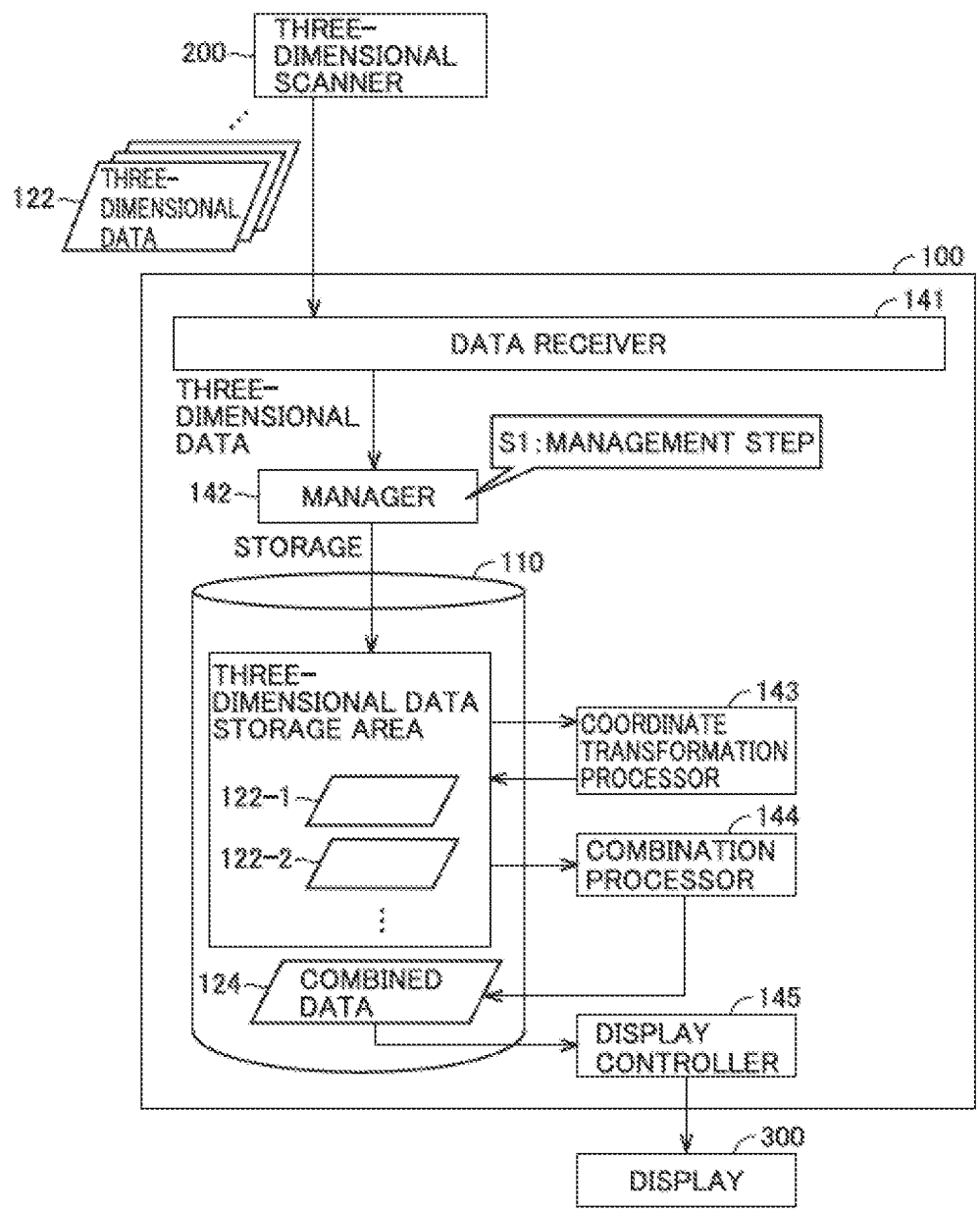
FIG. 8 is a diagram for illustrating processing dining measurement.
Figure 9:
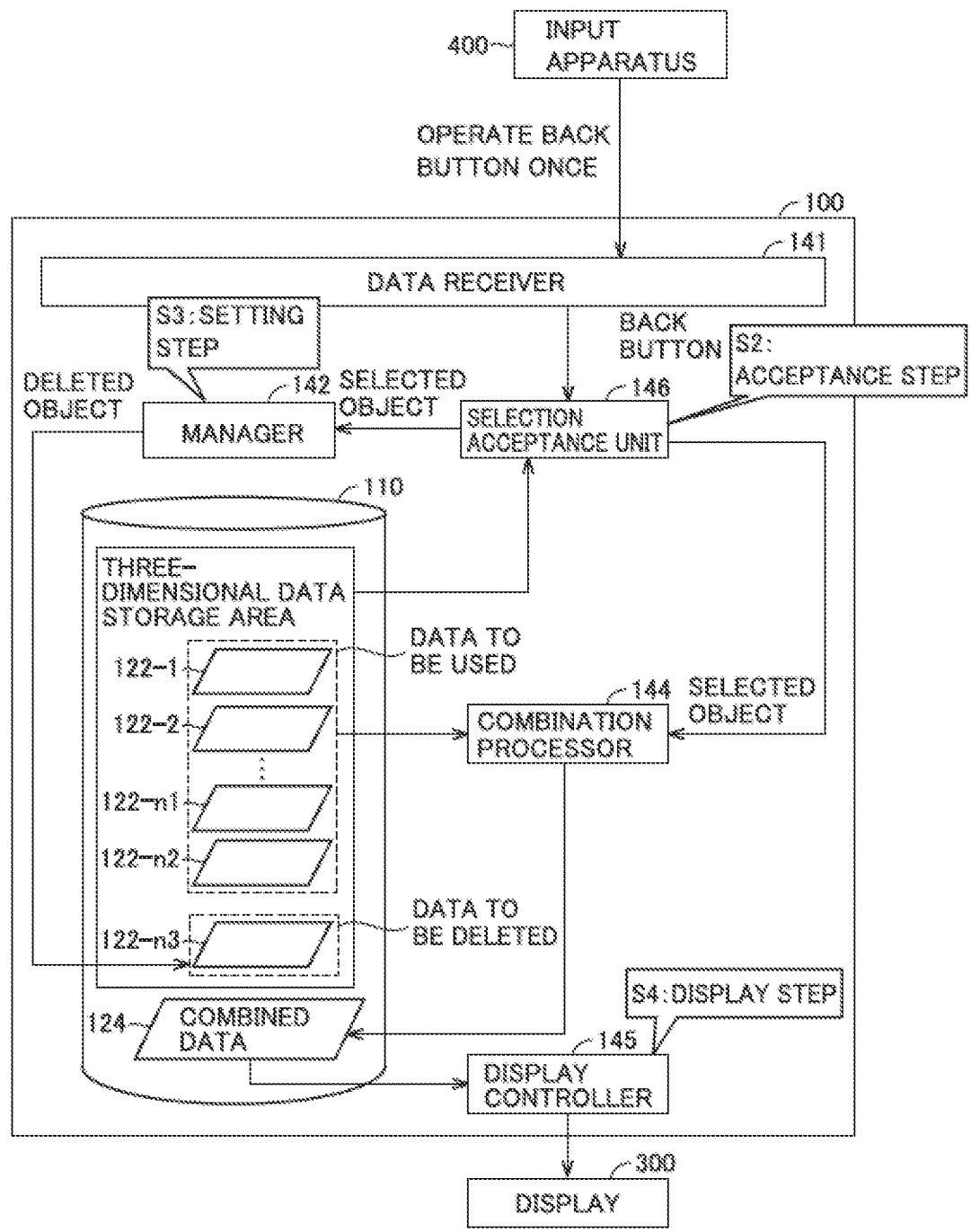
FIG. 9 is a diagram for illustrating processing during lion.

Processing during measurement and processing during suspension will be described with reference to FIGS. 8 and 9. FIG. 8 is a diagram for illustrating processing during FIG. 9 is a diagram for illustrating processing dining suspension.

Referring to FIG. 8, during measurement, scanner 200 sequentially transmits three-dimensional data 122 to information processing apparatus 100. Manager 142 causes sent three-dimensional data 122 to sequentially be stored in a data storage area within storage 110.

Coordinate transformation processor 143 sequentially performs registration processing onto stored three-dimensional data 122 and has three-dimensional data 122 subjected to coordinate transformation stored in storage 110 again. Coordinate transformation processor 143 may perform registration processing onto three-dimensional data 122 in the order of storage or in a prescribed order. Alternatively, coordinate transformation processor 143 may perform registration processing onto three-dimensional data 122 at a prescribed interval such as every other piece of three-dimensional data or every two pieces of three-dimensional data 122.

Combination processor 144 generates combined data 124 by combining three-dimensional data 122 from three-dimensional data 122 obtained first and subjected to coordinate transformation to latest three-dimensional data 122 subjected to coordinate transformation. Combination processor 144 sequentially combines three-dimensional data 122 subjected to coordinate transformation and sequentially generates combined data 124. Combination processor 144 generates combined data 124 each time coordinate transformation is completed.

Display controller 145 generates a three-dimensional image based on generated combined data 124 and controls display 300 to show the three-dimensional image. Each time combined data 124 is generated, display controller 145 generates the three-dimensional image and updates representation on display 300.

Figure 10:
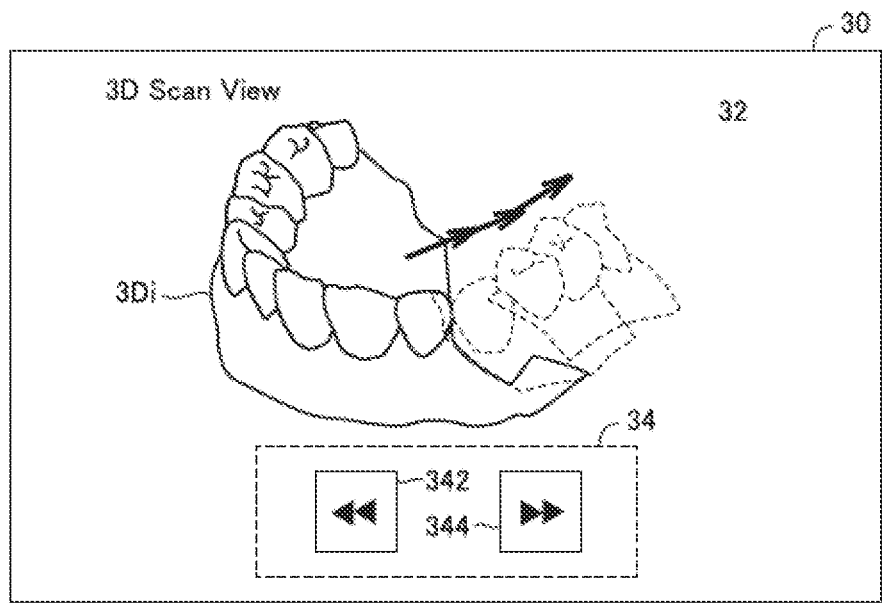
FIG. 10 shows exemplary on measurement screen 30 during measurement.

Update of the three-dimensional image during measurement will be described with reference to FIG. 10. FIG. 10 shows exemplary representation on measurement scan 30 during measurement. For example, as representation on display 300 is updated each time combined data 124 is generated as described above, three-dimensional images 3Di are successively generated in display area 32 along a direction shown with an arrow in FIG. 10. In display area 32, obtainment of three-dimensional data is shown.

Referring to FIG. 9, during suspension, data 122 is not transmitted from scanner 200. In the example shown in FIG. 9, it is assumed that data from three-dimensional data 122-*n*1 to tree-dimensional data 122-*n*3 are stored in garage 110. It is assumed that input apparatus 400 is operated and back button 342 in FIG. 2 is operated once. In the example shown in FIG. 2, description is given assuming that change is nude one by one in response to one operation onto back button 342.

In this case, selection acceptance unit 146 determines that last obtained three-dimensional data 122-*n*3 has been selected based on one operation onto back button 342. Each time back button 342 is operated, selection acceptance unit 146 changes a selected object one by one in the reverse order. Specifically, when back button 342 is operated again after back button 342 was operated once, selected three-dimensional data 122 is changed from three-dimensional data 122-*n*3 to three-dimensional data 122-*n*2.

In an example of an operation onto forward button 344 in FIG. 2, each time forward button 344 is operated, selection acceptance unit 146 changes a selected object in a unit of one piece or a plurality of pieces in the order of obtainment.

In the example shown in FIG. 9, back button 342 is operated once. Therefore, selection acceptance unit 146 notifies manager 142 and combination processor 144 of selection of three-dimensional data 122-*n*3.

Manager 142 sets as data to be deleted, data from selected three-dimensional data 122, the notification about which was given, to last obtained three-dimensional data 122. In the rile shown in FIG. 9, three-dimensional data 122-*n*3 is set as data to be deleted. As the data to be deleted is set, three-dimensional data 122-1 to three-dimensional data 122-*n*2 are set as data to be used.

Upon receiving the notification about the selected object from selection acceptance unit 146, combination processor 144 generates combined data 124, with three-dimensional data 122-1 to three-dimensional data 122-*n*2 included in the data to be used being adopted as data to be combined. Display controller 145 generates a three-dimensional image based on generated combined data 124 and controls display 300 to show the image.

Figure 11:
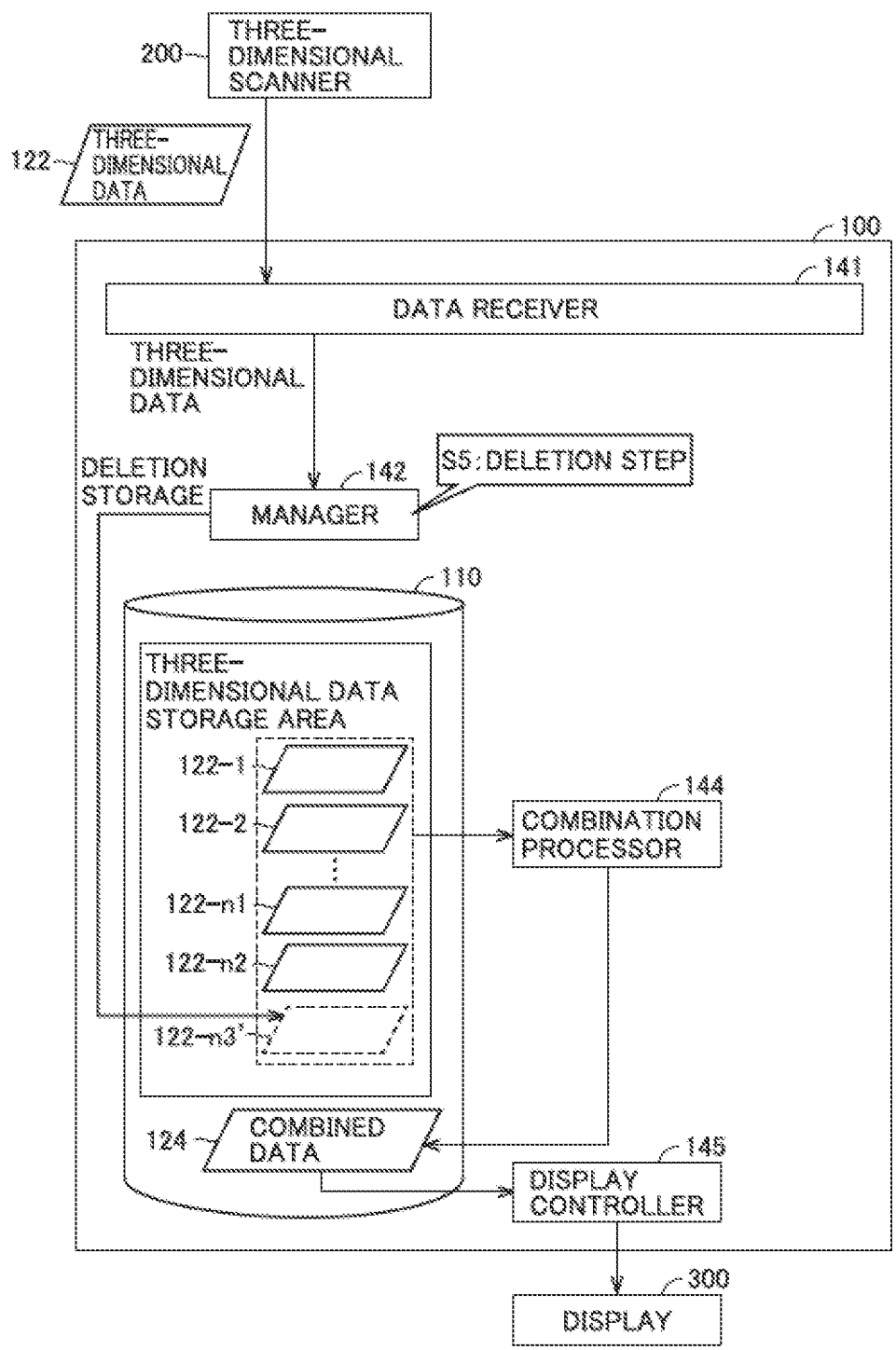
FIG. 11 is a diagram for illustrating processing at the time when data to be deleted shown in FIG. 9 is set as data to be deleted and thereafter measurement is resumed.

FIG. 11 is a diagram for illustrating processing when data to be deleted shown in FIG. 9 is set as data to be deleted and thereafter measurement is resumed. The example shown in FIG. 11 does not show coordinate transformation processor 143.

As measurement is resumed, manager 142 deletes the set data to be deleted (three-dimensional data 122-*n*3). When three-dimensional data 122 is newly sent from scanner 200, manager 142 causes obtained three-dimensional data 122 to successively be stored such that they follow three-dimensional data 122-*n*2.

Combination processor 144 then generates combined data 124 by combining three-dimensional data from that obtained three-dimensional data 122-1 to last obtained three-dimensional data 122-*n*2 among the data to be used with newly obtained three-dimensional data 122-*n*3'. Display controller 145 generates a three-dimensional image from generated combined data 124 and controls display 300 to show the three-dimensional image.

In other words, when the data to be deleted is set and thereafter three-dimensional data 122 is newly obtained, display controller 145 controls display 300 to show a three-dimensional image synthesized from the data to be used and newly obtained three-dimensional data 122-*n*3'.

Figure 12:
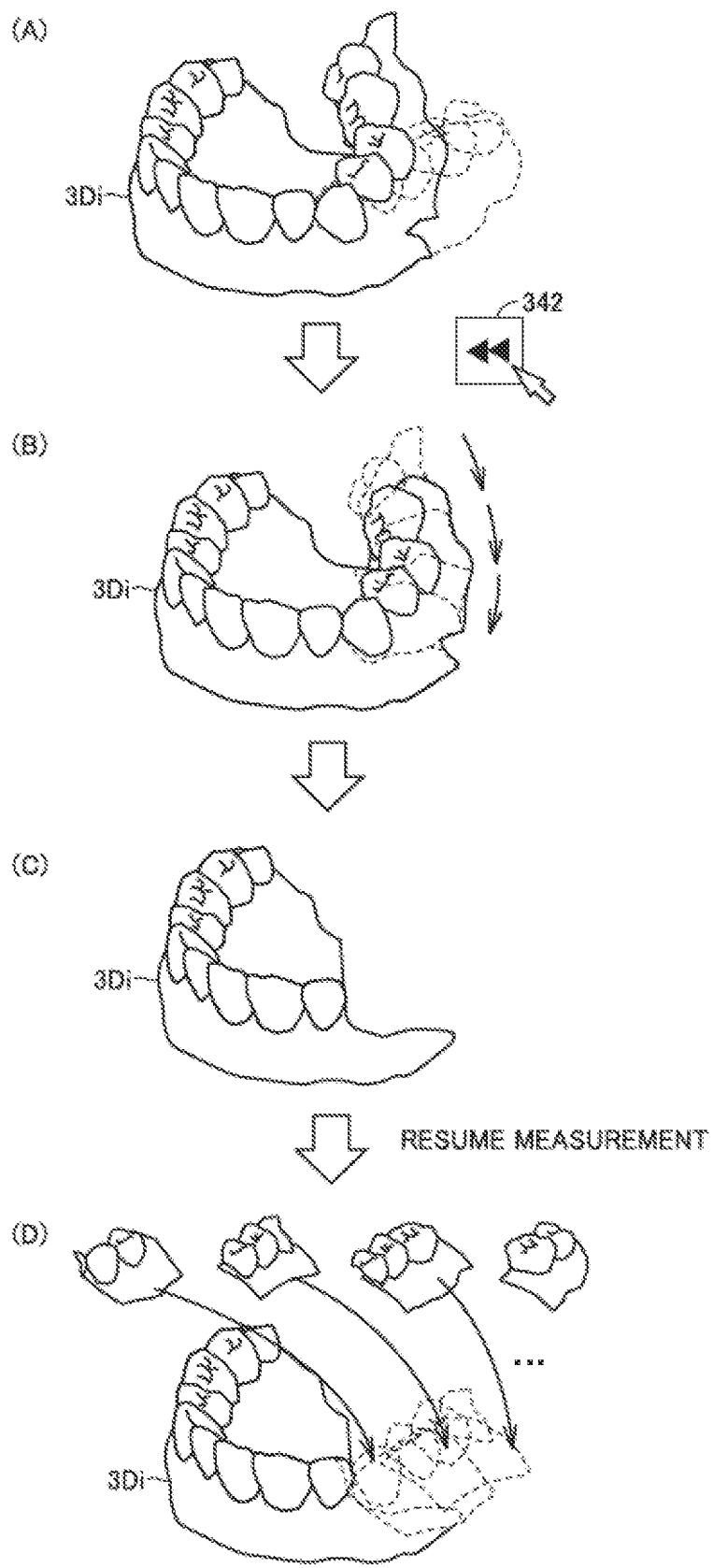
FIG. 12 is a diagram showing a three-dimensional image 3Di from after is resumed.

How three-dimensional data 3Di shown in display area 32 changes is described with reference to FIG. 12. FIG. 12 is a diagram showing three-dimensional image 3Di from after suspension of measurement until resumption of measurement. Three-dimensional image 3Di shown in display area 32 changes in the order of FIG. 12 (A), FIG. 12 (B), FIG. 12 (C), and FIG. 12 (D).

FIG. 12 (A) shows three-dimensional image 3Di shown in display area 32 when measurement is suspended. An image shown with a solid line is three-dimensional image 311 generated based an a result of measurement. An image shown with a dashed line represents an actual shape of an object. Though FIG. 12 (A) shows the image of the actual object with the dashed line for the sake of convenience of description, the image shown with the dashed line is not shown in display area 32.

In other words, FIG. 12 (A) shows a situation that registration processing failed due to some factor (a sudden operation or introduction of a movable object) during continuous scanning for obtaining three-dimensional data and a three-dimensional image far different from the actual shape was generated from a time point in continuous scanning. User 1 is assumed to have noticed failure in measurement by looking at three-dimensional image 3Di shown on display 300 and suspended measurement at the timing when representation of the three-dimensional image exhibited the state in FIG. 12 (A).

FIG. 12 (B) shows that input apparatus 400 is operated and back button 342 is operated a plurality of times to successively change a selected object from last obtained three-dimensional data 122 in the reverse order. Data to be deleted successively increases each time back button 342 is operated, and three-dimensional images successively disappear along a direction shown with an arrow in FIG. 12 (B).

User 1 can identify a range where measurement was normally conducted by checking three-dimensional image 3Di shown in display area 32 and determines data to be deleted (or data to be used) based on three-dimensional image 3Di. For example, user 1 is assumed to have identified three-dimensional data 122 included in three-dimensional image 3Di shown in FIG. 12 (C) as three-dimensional data 122 successfully obtained by normal measurement.

User 1 resumes measurement by operating acceptance portion 212. When measurement is resumed, as shown in FIG. 12 (D), a three-dimensional image generated based on obtained three-dimensional data 122 is successively added and a range where three-dimensional images 3Di are shown successively becomes larger.

Three-dimensional image 3Di is dais generated based on newly obtained three-dimensional data 122 instead of data to be deleted. In other words, by a simplified operation to simply repeat pressing of back button 342, user 1 can delete unnecessary data resulting from failure in scanning and thereafter continue subsequent scanning for obtaining remaining normal data.

[Data Processing Method]

A data processing method performed by information processing apparatus 100 will be described with reference to FIGS. 8, 9, and 11. The data processing method performed by information processing apparatus 100 includes step S1 to step S5 below.

Step S1: Step of managing three-dimensional data 122 in the order of obtainment by scanner 200 (management step)

Step S2: Step of accepting selected three-dimensional data 122 (acceptance step)

Step S3: Step of setting as data to be deleted, data from accepted selected three-dimensional data 122 to last obtained three-dimensional data 122 (setting step)

Step S4: Step of showing on display 300, a three-dimensional image generated by synthesizing data to be used except the set data to be deleted, among three-dimensional data 122 stored in the three-dimensional data storage area in storage 110 (display step)

Step S5: Step of deleting the set data to be deleted when the data to be deleted is set and thereafter three-dimensional data 122 is newly obtained (deletion step)

[Modification of Measurement Screen]

Figure 13:
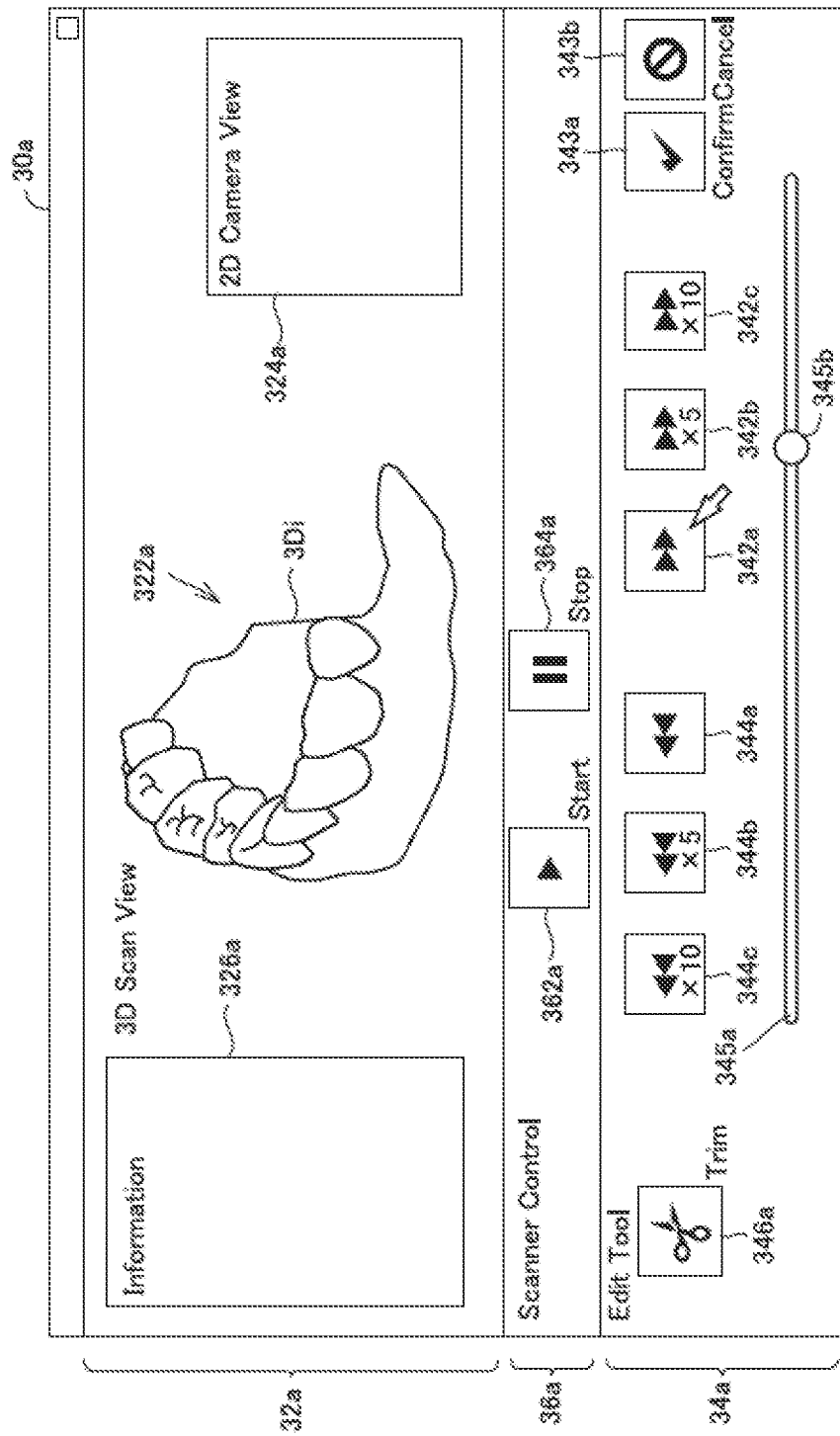
FIG. 13 shows an exemplary measurement screen 30a according to a modification.

FIG. 13 shows an exemplary measurement screen 30*a* according to a modification. Measurement screen 30*a* is different from measurement screen 30 in including a display area 32*a* instead of display area 32, including a selection area 34*a* instead of selection area 34, and further including a scanner control area 36*a*.

Display area 32*a* includes a synthesized image display area 322*a*, a camera image display area 324*a*, and an additional information display area 326*a*. Synthesized image display area 322*a* is an area common to display area 32 on measurement screen 30 for showing three-dimensional image 3Di. Representation in synthesized image display area 322*a* is updated by an operation onto an icon by user 1 and an operation onto scanner 200 by user 1.

Camera image display area 324*a* is an area for showing an image picked up by an image pick-up unit included in scanner 200. For example, user 1 can check a current measurement range by checking an image shown in camera image display area 324*a* during measurement.

Additional information display area 326*a* is an area where additional information is shown. The additional information includes information on object 2. The information on object 2 includes age of object 2, a past medical history of object 2, and contents of treatment for object 2.

Selection area 34*a* includes a back button (one frame) 342*a*, a back button (five frames) 342*b*, a back button (ten frames) 342*c*, a confirm button 343*a*, a cancel button 343*b*, a forward button (one frame) 344*a*, a forward button (five frames) 344*b*, a forward button (ten frames) 344*c*, a slider bar 345*a*, and a trim button 346*a*.

Back button (one frame) 342*a*, back button (five frames) 342*b*, back button (ten frames) 342*c*, forward button (one frame) 344*a*, forward button (five flames) 344*b*, and forward button (ten frames) 344*c* are each a selection tool for selecting three-dimensional data.

Back button (one frame) 342*a*, back button (five frames) 342*b*, and back button (ten frames) 342*c* are each a selection tool for successively changing selected three-dimensional data in the reverse order.

Back button (one frame) 342*a*, back button (five frames) 342*b*, and back button (ten frames) 342*c* are different from one another in unit of change in selected object in one operation. Back button (one frame) 342*a* is a selection tool for changing three-dimensional data one by one. Back button (five frames) 342*b* is a selection tool for changing three-dimensional data five by five. Back button (ten frames) 342*c* is a selection tool for changing three-dimensional data ten by ten.

Forward button (one frame) 344*a*, forward button (five frames) 344*b*, and forward button (ten frames) 344*c* are each a selection tool for changing selected three-dimensional data in the order of obtainment.

Forward button (one frame) 344*a*, forward button (five frames) 344*b*, and forward button (ten frames) 344*c* are different from one another in unit of change in selected object in one operation. Forward button (one frame) 344*a* is a selection tool for changing three-dimensional data one by one. Forward button (five frames) 344*b* is a selection tool for changing three-dimensional data five by five. Forward button (ten frames) 344*c* is a selection tool for changing three-dimensional data ten by ten.

Though the example shown in FIG. 13 exemplifies change one by one, five by five, and ten by ten, the number of pieces of data that can be changed in one operation is not limited as such. Though an example where three types of selection tools different in number of pieces of data to be changed are prepared is shown, at least one type of selection tool should only be prepared, and two types or at least four types of selection tools may be prepared.

A selected object may consecutively be changed in one operation. For example, when the back button is operated once, a selected object may automatically consecutively be changed in the order reverse to the order of obtainment and the selected object may be confirmed by operating a stop button once. Similarly, when the forward button is operated once, a selected object may automatically consecutively be changed in the order of obtainment and the selected object may be confirmed by operating the stop button.

Confirm button 343*a* is a button for confirming deletion. When confirm button 343*a* is operated, manager 142 of informs processing apparatus 100 deletes three-dimensional data 122 included in a range to be deleted.

Cancel button 343*b* is a button for resetting set data to be deleted. When cancel button 343*b* is operated, manager 142 of information processing apparatus 100 resets the data to be deleted. When cancel button 343*b* is operated, all pieces of obtained data are set as data to be used.

Slider bar 345*a* is an exemplary selection tool for changing a selected object. User 1 changes a selected object in the order of obtainment or in the order reverse to the order of obtainment by moving a slider 345*b* over slider bar 345*a*. For example, when slider 345*b* is moved to the right on the sheet plane, data to be used can be increased in the order of obtainment. When slider 345*b* is moved to the left on the sheet plane, data to be deleted can be increased in the order reverse to the order of obtainment.

Figure 14:
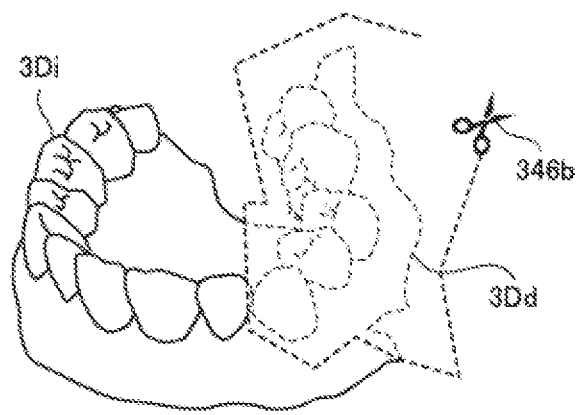
FIG. 14 is a diagram for illustrating a trimming function.

Trim button 346*a* is a selection tool for selecting a range to be deleted. FIG. 14 is a diagram for illustrating a trimming function. When trim button 346*a* is selected, a design of a pointer is changed to a design of scissors.

The range to be deleted can be selected by operating mouse 420 to move a pointer 346*b* over three-dimensional image 3Di shown in synthesized image display area 322*a*. When the range to be deleted is selected by using the trimming function, the range to be deleted is set for combined data 124 obtained by combining a plurality of pieces of three-dimensional data 122. Specifically, combined data 124 corresponding to an image to be deleted 3Dd included in the range to be deleted set in three-dimensional image 3Di is set as an object to be deleted Combined data 124 includes information of each of a plurality of coordinate points or a plurality of textured surfaces that define teeth to be scanned. Each of the plurality of coordinate points or the plurality of textured surfaces that define teeth to be scanned is set as an object to be deleted.

Some information processing apparatuses employed in conventional scanner systems have incorporated such a trimming function. In designating a range to be deleted by using the trimming function, however, a complicated operation such as a dragging operation with a mouse is required.

Measurement screen 30*a* according to the modification includes various buttons (back button (one frame) 342*a*) for setting an object to be deleted by selecting three-dimensional data 122 and trim button 346*a* for setting a range to be deleted by using the trimming function.

A method of setting an object to be deleted by selecting three-dimensional data 122 is excellent as an editing method in case of failure in scanning and suspension of measurement, because an object to be deleted can be set with a simplified operation. A selection method using the trimming function may be excellent as the editing method, for example, when fine modification is desired after measurement ends, because an arbitrary range to be deleted can be selected, although the operation is complicated Since measurement screen 30*a* according to the modification includes a button for selecting each method, user 1 can select an arbitrary method depending on a situation.

Scanner control area 36*a* includes a start button 362*a* and a stop button 364*a*. When start button 362*a* is selected, start of measurement is accepted and information processing apparatus 100 instructs scanner 200 to start measurement. When stop button 364*a* is selected, stop of measurement is accepted and information processing apparatus 100 instructs scanner 200 to stop measurements.

Though acceptance portion 212 provided in housing 210 of scanner 200 serves as an input unit for accepting start and stop of measurement in the embodiment, an icon on a graphical user interface (GUI) that can be selected through input apparatus 400 provided in information processing apparatus 100 may save as the input unit

[Modification of Method of Selecting Area to be Deleted]

In the embodiment, selection acceptance unit 146 accepts an operation by a user based on a signal provided in response to an operation onto input apparatus 400. In another example, selection acceptance unit 146 may accept an operation by the user based on a signal provided from the scanner in response to an operation onto the operation portion provided in the scanner.

Figure 15:
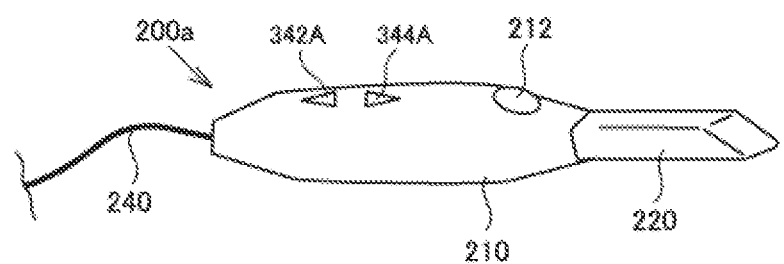
FIG. 15 is a schematic diagram of a scanner 200a according to a modification.

FIG. 15 is a schematic diagram of a scanner 200a according to a modification. Scanner 200a is different from scanner 200 in including a back button 342A and a forward button 344A as physical buttons.

A function of back button 342A corresponds to the function of back button 342 provided in measurement screen 30 in the embodiment. Similarly, a function of forward button 344A corresponds to the function of forward button 344 provided in measurement screen 30 in the embodiment.

When back button 342A is operated, scanner 200a sends a signal indicating the operation performed onto beck button 342A to information processing apparatus 100. When forward button 344A is operated, scanner 200a sends a signal indicating the operation performed onto forward button 344A to information processing apparatus 100.

When information processing apparatus 100 receives the signal indicating the operation performed onto beck button 342A, it performs processing the same as in the operation performed onto back button 342 described above. When information processing apparatus 100 receives the signal indicating the operation performed onto forward button 344A, it performs processing the same as in the operation onto forward button 344 described above.

Though an example where back button 342A and forward button 344A are each in a form of the button is described, the buttons are not limited as such and they may be replaced with other input devices provided on the scanner. For example, a touch pad may be provided on the scanner, and may be used with a function corresponding to back button 342 being allocated to swipe to the left, the function corresponding to forward button 344 being allocated to swipe to the right, and the function similar to an operation onto a slide bar being allocated to an operation corresponding to combination of press-and-hold and swipe. An operation may similarly be accepted by using a trackball, a cross-shaped key, an acceleration sensor, or an audio input device.

[Modification of Scanner]

Scanner 200 is of a hand-held type in the embodiment. The scanner, however, does not have to be of a hand-held type so long as positional relation thereof with a subject which is an object can relatively be changed. For example, the scanner system may include a movement mechanism that moves a subject and may change a measurment position by fixing the position of the scanner and moving the subject. The scanner system may be able to change positions of both of the scamper and the subject.

In the embodiment, scanner 200 is a three-dimensional scanner that obtains three-dimensional data 122. The scanner may be a camera that obtains two-dimensional data.

In the embodiment, scanner 200 is described as an intraoral scanner that obtains data on a shape of an object in the mouth cavity. The scanner can also be used for form measurement of the inside of the external ear without being limited to form measurement of an object (for example, a tooth) in the mouth cavity. The information processing apparatus in the present disclosure can also be used for processing data obtained by the scanner that measures a geometry of a human body.

[Manner of Representation of Data to be Deleted and Data to be Used]

In the embodiment, a three-dimensional image corresponding to three-dimensional data 122 set as data to be deleted is not displayed. A three-dimensional image corresponding to three-dimensional data 122 set as data to be deleted and a three-dimensional image corresponding to three-dimensional data 122 set as data to be used may be displayed in maniacs of representation different from each other. For example, a three-dimensional image corresponding to three-dimensional data 122 set as data to be deleted maybe shown with a dashed line and a three-dimensional image corresponding to three-dimensional data 122 set as data to be used may be shown with a solid line.

Though an embodiment has been described, it should be understood that the embodiment disclosed herein is illustrative and non-restrictive in every respect. The scope of the present disclosure is defined by the tams of the claims and is intended to include any modifications within the scope and meaning equivalent to the terms of the claims.

What is claimed is:

1. An information processing apparatus that processes data obtained by a scanner positionally variable in relation to a subject, the information processing apparatus comprising:
    management circuitry configured to manage a plurality of pieces of the data in an order of obtaining by the scanner;
    display controller circuitry configured to control a display apparatus to show a synthesized image generated by synthesizing the plurality of pieces of the data managed by the management circuitry; and
    input circuitry configured to accept an operation by a user,
    wherein
    the input circuitry is further configured to accept an operation to select data including at least one piece of data among the plurality of pieces of the data managed by the management circuitry,
    the management circuitry is further configured to set, from selected data of last obtained data, data to be deleted,
    the display controller circuitry is further configured to control the display apparatus to show the synthesized image, modified to exclude the data to be deleted, among the plurality of pieces of the data managed by the management circuitry,
    wherein the input circuitry is further configured to accept selection of data by accenting in operation via a data selection tool that allows selection of data in an order reverse to the order of obtaining,
    wherein as the data selection tool is operated, data to be selected is changed in a grow of one piece of the data or the plurality of pieces of the data in the reverse order, and
    wherein when the input circuitry accepts an operation to change the data to be selected for each group, the display controller circuitry is further configured to control the display apparatus to show the synthesized image each time the input circuitry accepts an operation to change the data to be selected.

2. The information processing apparatus according to claim 1, wherein
    when the input circuitry accepts the operation to select data and thereafter the scanner newly obtains data as newly obtained data, the display controller circuitry is further configured to control the display apparatus to show the synthesized image further including the newly obtained data.

3. The information processing apparatus according to claim 1, wherein
    when the management circuitry sets the data to be deleted and thereafter the scanner newly obtains data, the management circuitry is further configured to delete the data to be deleted set by the management circuitry.

4. The information processing apparatus according to claim 1, wherein the data selection tool includes a first tool with which the data to be selected is changed in a group of a first number and a second tool with which the data to be selected is changed in a group of a second number larger than the first number.

5. The information processing apparatus according to claim 1, wherein
the data selection tool includes a slider bar, and
as a slider on the slider bar is moved, data to be selected is changed in an obtaining order or in a reverse order.

6. The information processing apparatus according to claim 1, wherein
the scanner includes operation circuitry configured to be operable by the user, and
the input circuitry is further configured to accept an operation by the user by accepting a signal from the scanner generated by the operation via the operation circuitry.

7. The information processing apparatus according to claim 1, wherein
the scanner is an intraoral scanner that obtains a shape of an object in a mouth cavity as two-dimensional data or three-dimensional data.

8. A data processing method of processing data obtained by a scanner positionally variable in relation to a subject, the data processing method comprising:
managing a plurality of pieces of the data in an order of obtaining by the scanner,
accepting an operation to select at least one piece of data among a plurality of pieces of managed data as selected data;
setting, from the selected data of last obtained data, data to be deleted;
showing on a display apparatus, a synthesized image, modified to exclude the data to be deleted, among the plurality of pieces of the managed data,
wherein accepting selection of data by accepting an operation via a data selection tool that allows selection of data in an order reverse to the order of obtaining; and
as the data selection tool is operated, changing data to be selected in a group of one piece of the data or the plurality of pieces of the data in the reverse order,
wherein when an operation to change the data to be selected for each group is selected, controlling the display apparatus to show the synthesized image each time an operation to change the data to be selected is accepted.

9. The data processing method according to claim 8, further comprising
when the operation to select data is accepted and thereafter newly obtained data is obtained, controlling the display apparatus to show the synthesized image further including the newly obtained data.

10. The data processing method according to claim 8, further comprising:
when the data to be deleted is set and thereafter newly obtained data is obtained, deleting the set data to be deleted.

11. The data processing method according to claim 8, wherein
the data selection tool includes a first tool with which the data to be selected is changed in a group of a first number and a second tool with which the data to be selected is changed in a group of a second number larger than the first number.

12. The data processing method according to claim 8, wherein
the data selection tool includes a slider bar, and
as a slider on the slider bar is moved, data to be selected is changed in an obtaining order or in a reverse order.

13. The data processing method according to claim 8, wherein the scanner includes operation circuitry configured to be operable by the user, and
wherein the method further comprises:
accepting an operation by the user by accepting a signal from the scanner generated by the operation via the operation circuitry.

* * * * *